(12) United States Patent
Hart et al.

(10) Patent No.: US 10,517,642 B2
(45) Date of Patent: Dec. 31, 2019

(54) LAPAROSCOPIC TOOL WITH OBTURATOR

(71) Applicants: Stuart Richard Hart, Tampa, FL (US); Mario Alves Simoes, Pinellas Park, FL (US); Mark Antoine Zakaria, Baltimore, MD (US)

(72) Inventors: Stuart Richard Hart, Tampa, FL (US); Mario Alves Simoes, Pinellas Park, FL (US); Mark Antoine Zakaria, Baltimore, MD (US)

(73) Assignee: University of South Florida, Tampa, FL (US)

( * ) Notice: Subject to any disclaimer, the term of this patent is extended or adjusted under 35 U.S.C. 154(b) by 225 days.

(21) Appl. No.: 15/870,134

(22) Filed: Jan. 12, 2018

(65) Prior Publication Data

US 2018/0132893 A1    May 17, 2018

Related U.S. Application Data

(60) Division of application No. 14/740,623, filed on Jun. 16, 2015, now Pat. No. 9,901,374, which is a
(Continued)

(51) Int. Cl.
    *A61B 17/34* (2006.01)
    *A61B 17/42* (2006.01)
    *A61B 17/04* (2006.01)

(52) U.S. Cl.
    CPC ...... *A61B 17/3468* (2013.01); *A61B 17/0469* (2013.01); *A61B 17/42* (2013.01)

(58) Field of Classification Search
    CPC . A61B 17/3468; A61B 17/0469; A61B 17/42; A61B 2017/345
    See application file for complete search history.

(56) References Cited

U.S. PATENT DOCUMENTS 5,297,536 A    3/1994 Wilk
5,453,094 A    9/1995 Metcalf et al.
(Continued)

FOREIGN PATENT DOCUMENTS

WO    2011128392 A1    10/2011
WO    2013090909 A1    6/2013

OTHER PUBLICATIONS

Ashton-Miller and Delancey. Functional anatomy of the female pelvic floor. Ann N Y Acad Sci. 2007. vol. 1101: 266-296.
(Continued)

*Primary Examiner* — Anh T Dang
(74) *Attorney, Agent, or Firm* — Nicholas Pfeifer; Smith & Hopen, P.A.

(57) ABSTRACT

A laparoscopic device with obturator. The device facilitates extraction of specimens from a female subject's abdominal cavity through the subject's vagina by also facilitating the suturing of a mesh to the anterior and posterior walls of the subject's vagina. The device includes an elongate sheath that has a flat surface on the front, a curved shape on the back, and an inner port opening formed within the flat surface, where the port opening that enables introduction of instruments or removal of specimens from the peritoneal cavity. An internal obturator can be inserted into the sheath to reduce the size of the port opening into the peritoneal cavity, or can be used to close the inner port opening into the peritoneal cavity. The obturator and sheath can be utilized as firm surfaces against which a user can suture a sacrocolpopexy mesh to the anterior and posteriors vaginal walls.

10 Claims, 4 Drawing Sheets

Related U.S. Application Data continuation of application No. PCT/US2014/014894, filed on Feb. 5, 2014.

(60) Provisional application No. 61/760,983, filed on Feb. 5, 2013.

(56) References Cited

U.S. PATENT DOCUMENTS

| | | |
|---|---|---|
| 5,520,698 A | 5/1996 | Koh |
| 6,572,631 B1 | 6/2003 | McCartney |
| 7,377,897 B1 | 5/2008 | Kunkel et al. |
| 2010/0280368 A1 | 11/2010 | Can et al. |
| 2012/0330324 A1 | 12/2012 | Sauer |

OTHER PUBLICATIONS

Auyang et al., Natural orifice translumenal endoscopic surgery (NOTES((R))): a technical review. Surg Endosc. 2011. vol. 25: 3135-3148.

Bessler et al., Pure natural orifice transluminal endoscopic surgery (NOTES) cholecystectomy. Surg Endosc. 2010. vol. 24: 2316-2317.

Ceppa et al. Laparoscopic transgastric endoscopic retrograde endoscopy after Roux-en-Y gastric bypass. Surg. Obes. Relat. Dis. 2007. vol. 3: 21-24.

Dapri. Single access laparoscopic surgery: Complementary or alternative to NOTES? World J Gastrointest Surg. 2010. vol. 2 (No. 6): 207-9.

Park et al., Experimental studies of transgastric gallbladder surgery: cholecystectomy and cholecystogastric anastomosis. Gastrointest. Endosc. 2005. vol. 61 (No. 4): 601-606.

Ghezzi et al., Vaginal extraction of pelvic masses following operative laparoscopy. Surg Endosc. 2002. vol. 16: 1691-1696.

Hasson. A modified instrument and method for laparoscopy. Am J Obstet Gynecol. 1971. vol. 110 (No. 6): 886-887.

Jagannath et al. Peroral transgastric endoscopic ligation of fallopian tubes with long-term survival in a porcine model. Gastrointest. Endosc. 2005. vol. 61 (No. 3): 449-453.

Kantsevoy et al. Transgastric endoscopic splenectomy: is it possible? Surg. Endosc. 2006. vol. 20: 522-525.

Kaouk et al., NOTES transvaginal nephrectomy: first human experience. Urology. 2009. vol. 74: 5-8.

Lee et al., Total laparoscopic radical hysterectomy using Lee-Huang portal and McCartney transvaginal tube. The Journal of American Association of Gynecologic Laparoscopists. 2002. vol. 9 (No. 4): 536-540.

Litynski. Endoscopic surgery, the history, the pioneers. World J. Surg. 1999. vol. 23 (No. 8): 745-53.

Merrifield et al. Peroral transgastric organ resection: a feasibility study in pigs. Gastrointest. Endosc. 2006. vol. 63 (No. 4): 693-697.

Pearl and Ponsky. Natural orifice transluminal endoscopic surgery: past present and future. J Min. Am Surg. 2008. vol. 3 (No. 2): 43-46.

Peters et al., Laparoscopic transgastric endoscopic retrograde cholangiopancreatography for benign common bile duct structure after Roux-en-Y gastric bypass. Surg. Endosc. 2002. vol. 16: 1106.

Spuhler et al., A new vaginal extractor for laparoscopic surgery. J Am Assoc Gynecol Laparosc. 1994. vol. 1 (No. 4, Part 1): 401-404.

Stark and Benhidjeb. Natural Orifice Surgery: Transdouglas surgery—a new concept. JSLS. 2008. vol. 12: 295-298.

Wagh et al., Survival studies after endoscopic transgastric oophorectomy and tubectomy in a porcine model. Gastrointest. Endosc. 2008. vol. 63 (No. 3): 473-478.

Wagh and Thompson. Surgery insight: natural orifice transluminal endoscopic surgery—an analysis of work to date. Gastr. & Hept. 2007. vol. 4 (No. 7): 386-392.

International Search Report and Written Opinion for PCT/US2014/014894 (filing date: Feb. 5, 2014) dated Nov. 13, 2014; Applicant: University of South Florida.

International Preliminary Report on Patentability for PCT/US2014/014894 (filing date: Feb. 5, 2014) with a priority date of Feb. 5, 2013; Applicant: University of South Florida.

LAPAROSCOPIC TOOL WITH OBTURATOR

CROSS-REFERENCE TO RELATED APPLICATIONS

This nonprovisional application is a divisional of U.S. Nonprovisional patent application Ser. No. 14/740,623, entitled "Laparoscopic Tool with Obturator", filed Jun. 16, 2015, which is a continuation of PCT Patent Application No. PCT/US2014/014894, entitled "Laparoscopic Tool with Obturator", filed Feb. 5, 2014, which claims priority to U.S. Provisional Patent Application No. 61/760,983, entitled "Vaginal Port with Obturator", filed Feb. 5, 2013, all of which are incorporated herein by reference in their entireties.

BACKGROUND OF THE INVENTION

1. Field of the Invention

This invention relates, generally, to laparoscopic instrumentation and use. More particularly, it relates to endoscopic devices for use in transvaginal laparoscopic surgeries, such as procedures to correct prolapse in female patients (e.g., sacrocolpopexy, sacrohysteropexy, and similar procedures).

2. Description of the Prior Art

Minimally invasive laparoscopic techniques have been developed in order to avoid large skin incisions associated with traditional surgery, involving use of small incisions (each about 5-12 mm in diameter) in the patient's abdominal wall, in which surgical instruments are inserted. These surgical instruments may be used to dissect and remove tissues and organs (i.e., specimens) that can be several centimeters in diameter. Such minimally invasive surgical techniques have been evolving for more than 100 years, since Georg Kelling performed the first experimental laparoscopy in 1901. (Litynski, G. Endoscopic surgery, the history, the pioneers. World J. Surg. 1999 August; 23(8): 745-53). These minimally invasive laparoscopic surgeries result in less post-operative pain, quicker recovery and an improved cosmetic appearance for patients compared to traditional laparotomy. Currently, hybrid procedures combining flexible endoscopy and laparoscopy, such as intraoperative enteroscopy and laparoscopic-assisted endoscopic retrograde cholangiopancreatography, are performed in increasing numbers. (Ceppa, F., et al. Laparoscopic transgastric endoscopic retrograde endoscopy after Roux-en-Y gastric bypass. Surg. Obes. Relat. Dis. 3: 21-24 2007; Peters, M., et al. Laparoscopic transgastric endoscopic retrograde cholangiopancreatography for benign common bile duct structure after Roux-en-Y gastric bypass. Surg. Endosc. 16:1106 2002).

One limitation, however, has been the removal of pathologic specimens that are larger than the port sites used to perform these surgeries. Consequently, these large specimens typically must be removed from the abdominal cavity by cutting or morcellating them within the abdominal cavity or by making an incision in the abdominal wall that is large enough to accommodate removal of the large specimen.

Further, laparoscopic instruments are typically confined to fit within these port sizes, thus limiting development of larger and more efficient minimally invasive surgical devices. A typical umbilicus laparoscopic port incision is no larger than 15 mm, and other support incisions are usually much smaller. Larger incisions lead to more scarring and the potential for hernia formation. Therefore, the tools used for laparoscopy are small in size to fit these incision limitations.

Recently, surgeons have taken advantage of natural orifices (vagina, rectum, urethra, and gastrointestinal tract) to perform Natural Orifice Transluminal Endoscopic Surgery (NOTES) procedures with good results (Bessler, M.; Gumbs, A. A.; Milone, L.; Evanko, J. C.; Stevens, P.; Fowler, D. Video. Pure natural orifice transluminal endoscopic surgery (NOTES) cholecystectomy. Surg Endosc 24: 2316-2317; 2010; Kaouk, J. H.; White, W. M.; Goel, R. K.; Brethauer, S.; Crouzet, S.; Rackley, R. R.; Moore, C.; Ingber, M. S.; Haber, G. P. NOTES transvaginal nephrectomy: first human experience. Urology 74: 5-8; 2009; Pearl, J., Ponsky, J., Natural orifice transluminal endoscopic surgery: past present and future. J Min. Acc. Surg. 3:2 43-46 2008; Wilk, P., U.S. Pat. No. 5,297,536). NOTES has been used for diagnostic and therapeutic procedures including organ removal, though current articulating instruments for use with NOTES are disposable, increasing costs compared to standard laparoscopic procedures, and removal of large tumors or solid organs cannot be performed using NOTES (Dapri, Single access laparoscopic surgery: Complementary or alternative to NOTES? World J Gastrointest Surg. 2010 Jun. 27; 2(6): 207-9). Advantages of NOTES include cosmetic results; reduced anesthesia requirements; faster recovery and shorter hospital stays; decreased abdominal trauma and therefore potential complications of transabdominal wound infections, such as hernias; less need for immunosuppression and pain killers; and better postoperative pulmonary and diaphragmantic function.

NOTES has been extensively studied in animal models, with tubal ligation, gallbladder surgery, oophorectomy, hysterectomy, gastrojejunostomy, and splenectomy having been described. (Jagannath, S., et al. Peroral transgastric endoscopic ligation of fallopian tubes with long-term survival in a porcine model. Gastrointest. Endosc. 61: 449-453 2005; Experimental studies of transgastric gallbladder surgery: cholecystectomy and cholecystogastric anastomosis. Gastrointest. Endosc. 61: 601-606 2005; Wagh, M. et al., Survival studies after endoscopic transgastric oophorectomy and tubectomy in a porcine model. Gastrointest. Endosc. 63: 473-478 2008; Merrifield, B., et al. Peroral transgastric organ resection: a feasibility study in pigs. Gastrointest. Endosc. 63: 693-697 2006; Kantsevoy, S., et al. Transgastric endoscopic splenectomy: is it possible? Surg. Endosc. 20: 522-525 2006). These surgical procedures are promising advances, due to the potential to eliminate traditional surgical complications, like postoperative abdominal wall pain, wound infections, hernias, adhesions, and impaired immune function. (Wagh, M., Thompson, C. Surgery insight: natural oriice transluminal endoscopic surgery—an analysis of work to date. Gastr. & Hept. 4:7 386-392 2007). Further, NOTES procedures may be performed under conscious sedation and not general anesthesia. (Pearl, J., Ponsky, J., Natural orifice transluminal endoscopic surgery: past present and future. J Min. Acc. Surg. 3:2 43-46 2008). The transluminal approach could be particularly important for morbidly obese patients and others at high risk for standard surgery.

The vagina is an ideal portal to access the abdominal cavity for women undergoing minimally invasive laparoscopic surgery, and is regaining interest in the surgical community (Auyang, E. D.; Santos, B. F.; Enter, D. H.; Hungness, E. S.; Soper, N. J. Natural orifice transluminal endoscopic surgery (NOTES®): a technical review. Surg Endosc 25: 3135-3148; 2011; Stark, M.; Benhidjeb, T.

Natural Orifice Surgery: Transdouglas surgery—a new concept. JSLS 12: 295-298; 2008) for peritoneal access. According to some computer generated models (Ashton-Miller, J. A.; DeLancey, J. O. Functional anatomy of the female pelvic floor. Ann N Y Acad Sci 1101: 266-296; 2007), its elasticity allows stretching to accommodate dimensions greater than three times its resting state. The posterior portion of the vagina also directly communicates with the abdomen through only a few tissue layers, and when placed on stretch, is distant from vital anatomic structures. A laparoscopic port utilizing transvaginal access would increase the surgeon's access to the abdominal cavity and provide a much larger incision site, without the concerns for hernia formation and scarring. Additionally, transvaginal removal of large specimens enables minimally invasive laparoscopic surgery without the need for morcellation within the abdominal cavity or large incisions in the abdominal wall to remove the specimens, enabling minimal scarring and faster recovery following surgery. Accordingly, transvaginal NOTES is considered one of the safest and feasible methods for clinical application. Totally transvaginal cholecystectomy has been experimentally performed without using laparoscopic assistance.

Ghezzi et al. (Ghezzi, F.; Raio, L.; Mueller, M. D.; Gyr, T.; Buttarelli, M.; Franchi, M. Vaginal extraction of pelvic masses following operative laparoscopy. Surg Endosc 16: 1691-1696; 2002.) and Spuhler et al. (Spuhler, S. C.; Sauthier, P. G.; Chardonnens, E. G.; De Grandi, P. A new vaginal extractor for laparoscopic surgery. J Am Assoc Gynecol Laparosc 1: 401-404; 1994) described devices for the extraction of pelvic masses following laparoscopy. These devices utilized a metal shaft with a fitted rubber ball to provide vaginal occlusion and prevent loss of pneumoperitoneum. Another device developed in Australia and marketed by Gynetech Pty Ltd, uses a similar hollow tube placed in the vagina (McCartney, A. J. Transvaginal tube as an aid to laparoscopic surgery. Google Patents; 2003). The design of this device is such that the tube fits around the cervix to distinguish the cervicovaginal junction, similar to the Koh colpotomy cup already in use for hysterectomy procedures (Koh, C. H. Simplified total laparoscopic hysterectomy method employing colpotomy incisions. Google Patents; 1996).

However, there is a need for an improved device that utilizes the vagina as an access to the peritoneal cavity for the introduction of laparoscopic surgical devices or implants, or the extraction of pathologic specimens. Accordingly, what is needed in the art is devices that permit enhanced access to the abdomen during surgery. However, in view of the art considered as a whole at the time the present invention was made, it was not obvious to those of ordinary skill how the art could be advanced.

While certain aspects of conventional technologies have been discussed to facilitate disclosure of the invention, Applicants in no way disclaim these technical aspects, and it is contemplated that the claimed invention may encompass one or more of the conventional technical aspects discussed herein.

The present invention may address one or more of the problems and deficiencies of the prior art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

BRIEF SUMMARY OF THE INVENTION

The long-standing but heretofore unfulfilled need for an improved transvaginal laparoscopic surgical device and method is now met by a new, useful, and nonobvious invention.

In an embodiment, the current invention is a laparoscopic tool. The laparoscopic tool includes a tubular or ovoid elongate sheath having a proximal end (closer to the operator or clinician) and a distal end (closer to the patient or subject). The sheath has a semi-flat longitudinal side and a curved longitudinal side enclosing an interstitial space within the sheath. A port opening is formed in the semi-flat side at the distal end of the sheath. The port opening has a length that is aligned or coplanar with the semi-flat side. The curved side meets or intersects the semi-flat side at a point distal to the port opening. The laparoscopic tool further includes an elongate obturator that can be inserted into the interstitial space of the sheath. The obturator includes a shaft disposed within the interstitial space when the obturator is inserted into the sheath. The obturator further includes a head coupled to the distal end of the shaft, where the head is positioned within the distal end of the sheath when the obturator is inserted into the sheath. The head of the obturator has a substantially flat side and a curved side, such that the substantially flat side fills at least a portion of the space or void provided by the port opening within the semi-flat side of the sheath. The curved side of the obturator head is positioned along and within the curved side of the sheath.

A handle may optionally be connected to the proximal end of the sheath for controlling the laparoscopic tool.

A push-pull knob may optionally be coupled to the proximal end of the obturator shaft for pushing or pulling the obturator into and out of the sheath.

The curved side of the obturator head may optionally have a curvature that is substantially similar to the curvature of the curved longitudinal side of the sheath at the distal end of the sheath.

The obturator shaft may optionally have a diameter or width that is smaller than the width of the obturator head.

The port opening may have a teardrop shape, such that it is wider at its distal-most point and narrower at its proximal-most point.

In a separate embodiment, the current invention is a laparoscopic tool for suturing a sacrocolpopexy mesh to the anterior and posterior vaginal walls during treatment of vaginal prolapse in a female patient. The laparoscopic tool includes a tubular or ovoid elongate sheath having a proximal end (closer to the operator or clinician) and a distal end (closer to the patient or subject). The sheath has a semi-flat longitudinal side and a curved longitudinal side enclosing an interstitial space within the sheath. A teardrop-shaped port opening is formed in the semi-flat side at the distal end of the sheath, such that it is wider at its distal-most point and narrower at its proximal-most point. The port opening has a length that is aligned or coplanar with the semi-flat side. The curved side meets or intersects the semi-flat side at a point distal to the port opening. The laparoscopic tool further includes an elongate obturator that can be inserted into the interstitial space of the sheath. The obturator includes a shaft disposed within the interstitial space when the obturator is inserted into the sheath. The obturator further includes a head coupled to the distal end of the shaft, where the head is positioned within the distal end of the sheath when the obturator is inserted into the sheath. The obturator shaft has a diameter or width that is smaller than the width of the obturator head. The head of the obturator has a substantially flat side and a curved side, such that the substantially flat side fills at least a portion of the space or void provided by the port opening within the semi-flat side of the sheath. The curved side of the obturator head is positioned along and within the curved side of the sheath. The curvature of the curved side of the obturator head is substantially similar to the curvature of the curved longitudinal side of the sheath at the distal end of the sheath. The laparoscopic tool further includes a handle connected to the proximal end of the sheath for controlling the laparoscopic tool. The laparoscopic tool further includes a push-pull knob coupled to the proximal end of the obturator shaft for pushing or pulling the obturator into and out of the sheath.

In a separate embodiment, the current invention is a method of treating pelvic organ prolapse in a female patient. A laparoscopic tool is inserted into a vagina of the patient, where the laparoscopic tool includes an elongate sheath having a semi-flat side and a curved side. A port opening is formed in the semi-flat side. When the laparoscopic tool is inserted into the vagina, an incision is made through the port opening where desired by the user (e.g., operator, clinician, etc.). At this point, the peritoneal cavity of the patient can be accessed through the incision. An elongate obturator is inserted through the sheath to reduce the size of the port opening. The obturator includes a shaft and a head that is coupled to the distal end of the shaft. The head has a substantially flat side and a curved side, where the substantially flat side is positioned substantially within the port opening and the curved side is positioned along and within the distal end of the curved side of the sheath. A sacrocolpopexy mesh is sutured (e.g., via interrupted permanent sutures, autosuture device) to the vagina using one or both of the following: the substantially flat side of the obturator, and the curved side of the sheath. These can be used as one or more firm surfaces against which the user can suture the sacrocolpopexy mesh to the vagina.

The sacrocolpopexy mesh may optionally be a Y-shaped mesh with two (2) branches on an end of the Y-shaped mesh. In a further embodiment, during insertion of the laparoscopic tool, the semi-flat side of the sheath and the port opening are positioned against the posterior vaginal wall of the patient. As such, the curved side of the sheath is positioned against the anterior vaginal wall of the patient. In this position, one branch of the Y-shaped mesh can be sutured against the posterior vaginal wall using the substantially flat side of the obturator head as a firm surface against which the user can suture the branch of the Y-shaped mesh to the posterior vaginal wall. The other branch of the Y-shaped mesh can be sutured against the anterior vaginal wall using the curved side of the obturator head as a firm surface against which the user can suture the branch of the Y-shaped mesh to the anterior vaginal wall.

The incision may optionally be made in the posterior cul-de-sac (i.e., Pouch of Douglas, recto-uterine pouch) of the patient through the port opening of the laparoscopic tool in order to access the peritoneal cavity of the patient.

The laparoscopic tool may optionally include a push-pull knob may optionally be coupled to the proximal end of the obturator shaft for pushing or pulling the obturator into and out of the sheath.

The curved side of the obturator head may optionally have a curvature that is substantially similar to the curvature of the curved longitudinal side of the sheath at the distal end of the sheath.

The obturator shaft may optionally have a diameter or width that is smaller than the width of the obturator head.

The port opening may have a teardrop shape, such that it is wider at its distal-most point and narrower at its proximal-most point.

These and other important objects, advantages, and features of the invention will become clear as this disclosure proceeds.

The invention accordingly comprises the features of construction, combination of elements, and arrangement of parts that will be exemplified in the disclosure set forth hereinafter and the scope of the invention will be indicated in the claims.

BRIEF DESCRIPTION OF THE DRAWINGS

For a fuller understanding of the nature and objects of the invention, reference should be made to the following detailed disclosure, taken in connection with the accompanying drawings, in which.

DETAILED DESCRIPTION OF THE PREFERRED EMBODIMENT

Figure 1:
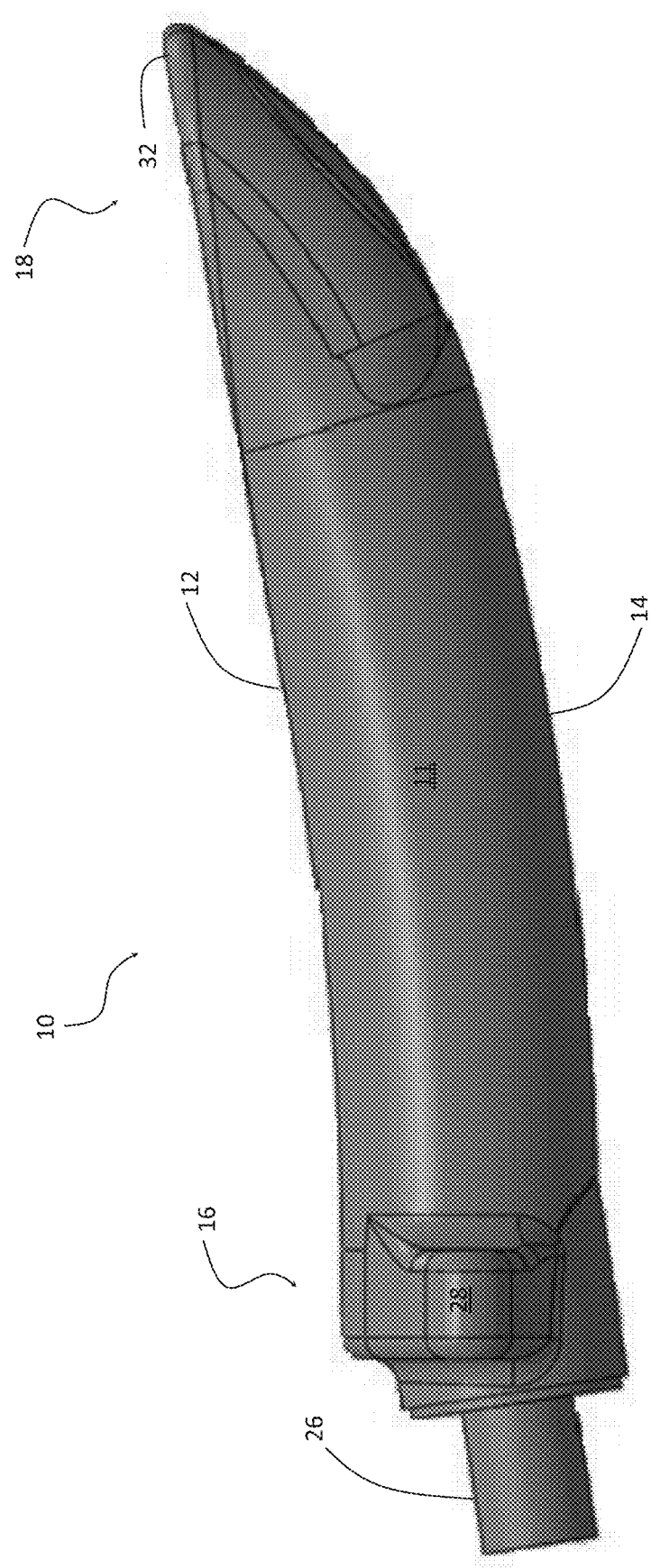
FIG. 1 is a side view of a transvaginal laparoscopic tool with obturator according to an embodiment of the current invention.

In the following detailed description of the preferred embodiments, reference is made to the accompanying drawings, which form a part thereof, and within which are shown by way of illustration specific embodiments by which the invention may be practiced. It is to be understood that other embodiments may be utilized and structural changes may be made without departing from the scope of the invention.

For female patients, it is possible to take advantage of the fact that the abdominal cavity can be accessed through the vagina. Furthermore, the vagina has sufficient elasticity, allowing it to stretch to accommodate removal of large specimens or insertion of larger instruments than typically seen in laparoscopic procedures through the abdomen of the patient. The underutilization of the vagina as a portal for use during laparoscopic surgery may be due, in part, to the paucity of medical devices and instruments designed for this mode of access. While there are some vaginal colpotomizer rings and uterine manipulators commercially available, there are few effective devices (e.g., PCT Application No. PCT/US2012/070147, which is incorporated herein by reference) specifically designed for use in the vagina during laparoscopic surgery.

This invention involves a device used during laparoscopic surgery that is used to extract tissues or organs, referred herein as "specimens", from a woman's abdominal cavity through the woman's vagina, or to introduce devices or implants into the abdomen during surgery, or to provide a firm surface for suturing. The device shaft was designed to accommodate the average dimensions of the animal's vagina, such as a human, with both a straight and curved design to allow the surgeon optimal flexibility when manipulating the device during actual use in laparoscopic surgical procedures. The apparatus of the current invention includes a transvaginal laparoscopic tool with obturator that enables an operator, user, or clinician to perform minimally invasive surgery using the advantages of a vaginal entry into the peritoneal cavity, while also having a shape that is ideal for suturing mesh to the vagina during prolapse surgery.

In particular, a sacrocolpopexy procedure typically uses a Y-shaped mesh, or other configuration of mesh, which is sutured to the anterior and/or posterior vaginal wall. The mesh is sutured to the anterior vaginal wall most effectively when a solid, semi-flat surface is used as a base or backboard in the vagina, which enables the vagina to be stretched to maximize anterior vaginal wall surface area. In this way, the mesh can lay flat on the anterior vaginal wall during suturing. It is often quite difficult to suture the mesh on the posterior vaginal wall of a patient due to the natural angle of the vagina, which lays flat over the pelvic floor.

It is also quite difficult to access deep in the posterior cul-de-sac and suture the mesh to the perineal body. The curve on the back of the device allows the vagina to be lifted upwards and out of the posterior cul-de-sac, thereby enabling safe entry of the inner port opening of the laparoscopic tool into the peritoneal cavity, and also enabling the surgeon to suture mesh to the posterior vaginal wall and to the perineal body, using one multipurpose transvaginal laparoscopic tool according to the current invention.

The obturator can be inserted into the inner port during suturing of the mesh to the posterior vaginal wall during a sacrocolpopexy procedure, such that the surgeon can suture on a solid surface. The obturator can also be used to reduce the caliber of the inner port opening, which can allow different size instruments to be inserted into the peritoneal cavity without having too large or small of an opening.

Certain embodiments of the current invention include a device used during laparoscopic surgery that enables the surgeon to extract tissues or organs (i.e., "specimens") from a woman's abdominal cavity through the woman's vagina, but is also customizable with multiple size internal obturators. As seen in FIGS. 1-4, the device, according to an embodiment of the current invention, can include a transvaginal laparoscopic tool having a flat surface on the front, a curved shape on the back, and an inner port that enables introduction of instruments or removal of specimens from the peritoneal cavity. An internal obturator can be positioned in the inner port to reduce the size of the distal opening into the peritoneal cavity, or can be used to close the inner port opening into the peritoneal cavity. By closing the inner port opening with the obturator, the transvaginal laparoscopic tool has an ideal configuration for performance of a sacrocolpopexy procedure. It allows the surgeon to suture the Y-shaped mesh to the front wall of the vagina using the front vaginal port flat surface, and to the back wall of the vagina and perineal body using the back curved vaginal port surface since this is an ideal configuration to access deep in the posterior cul-de-sac.

Currently, the prior art fails to teach any transvaginal laparoscopic tool that enables removal of abdominal/pelvic masses while also allowing introduction of instruments into the peritoneal cavity. Also, current laparoscopic ports are limited in size, typically to 5 to 12 mm, since larger ports require larger incisions in the abdominal wall, which increases scarring, post-op pain and risk of hernia formation. Using embodiments of the current invention with the distensibility characteristics of the vagina, a significantly larger port can be designed to enable greater access into the peritoneal cavity than is possible through traditional laparoscopic ports placed in the abdominal wall. This enables development of larger laparoscopic instruments, while also allowing the surgeon to remove significantly larger masses without having to extend abdominal wall incisions or use a morcellator which has inherent risks of injury to surrounding organs or blood vessels.

The major challenges of performing a sacrocolpopexy procedure is suturing the Y-shaped mesh to a flat surface on the front of the vagina, and then accessing deep in the posterior cul-de-sac to suture the Y-shaped mesh in this area. The transvaginal laparoscopic tool with obturator device, according to the current invention, is unique in that the shape is ideally designed for the sacrocolpopexy procedure, while also working as a transvaginal laparoscopic tool. In this way, a wide variety of medical procedures can be performed utilizing one vaginal port.

Additionally, the obturator can be designed to enable a small needle-like device to be inserted through the vagina to hold the Y-shaped sacrocolpopexy mesh in place during suturing of the mesh to the anterior and/or posterior walls of the vagina. This can also serve to stabilize the mesh in correct position on the vaginal wall, a task that solves another challenging aspect of the procedure.

The laparoscopic tool of the current invention, or each component thereof, can be formed of any suitable material, for example including, but not limited to, surgical steel, plastic, and titanium.

Example 1

The laparoscopic instrument may safely facilitate entry into the abdominal cavity during laparoscopic surgery. Traditionally, peritoneal access has been obtained by a transabdominal approach. The Veress needle, which was originally developed to perform pleurodesis in tuberculosis patients, is commonly used to access the abdominal cavity and provide pneumoperitoneum. One disadvantage is the blind placement of the needle into the abdomen and the risk of injury to adjacent organs and blood vessels.

One method, reported in 1971 by Harry Hasson and now called the open technique, has overcome this blind entry to access the peritoneal cavity (Hasson, H. M. A modified instrument and method for laparoscopy. Am J Obstet Gynecol 110: 886-887; 1971). Also, some advances in optical trocar design have allowed for visualizing entry with the use of the laparoscope that often, but not necessarily, requires prior pneumoperitoneum. However, these techniques continue to use trans-abdominal entry, most commonly through the umbilicus, with the attributed risk for vital organ and vascular injury using this approach.

The laparoscopic instrument can allow for direct entry into the posterior cul-de-sac, or Pouch of Douglas, through the posterior portion of the vagina, which is perhaps the safest access site into the abdominal cavity. As the vagina is elastic, the posterior apex of the vagina is displaced away from the rectosigmoid, and provides a safe entry even in difficult surgical procedures. Combined with the relative ease of repair of the incision, colpotomy access to the abdominal cavity is safe for patients and convenient for surgeons.

FIGS. 1-4 depict a laparoscopic tool, generally denoted by the reference numeral 10, according to an exemplary embodiment of the current invention. Laparoscopic tool 10 has a generally circular or ovoid cross-section. As seen in FIG. 1, laparoscopic tool 10 includes elongate sheath 11 with interstitial space 13 therewithin. Elongate sheath 11 includes a first side, denoted by the reference numeral 12, and a second side, denoted by the reference numeral 14. Laparoscopic tool 10 further includes a proximal end, generally denoted by the reference numeral 16, and a distal end, generally denoted by the reference numeral 18. As used herein, the term "proximal" refers to a location that, during normal use, is closer to the operator or clinician using the device and farther from the patient in connection with whom the device is used. Conversely, the term "distal" refers to a location that, during normal use, is farther from the clinician using the device and closer to the patient in connection with whom the device is used.

First side 12 is semi-flat along its surface and along port opening 30. When laparoscopic tool 10 is placed within a vagina, first side 12 and port opening 30 are positioned along or otherwise facing the posterior vaginal wall of the patient to facilitate access into the peritoneum through an appropriate incision in the posterior cul-de-sac (i.e., Pouch of Douglas) through port opening 30. First side 12 can be slightly curved to accommodate the undulations and form of the posterior vaginal wall.

Laparoscopic tool 10 further includes port opening 30 on its distal end 18 within first side 12 of elongate sheath 11. Interstitial space 13 is in open communication with the external environment (i.e., exterior space) through port opening 30. A retractable or removable cover (not shown) can be positioned on port opening 30 to close off interstitial space 13 when needed. Second side 14 is curved so as to meet first side 12 at rounded lip 32. This type of configuration permits port opening 30 to be aligned with first side 12. Rounded lip 32 forms the distal-most point of laparoscopic tool 10 and thus helps prevent laparoscopic tool 10 from harming anatomical structures within the patient.

Figure 2:
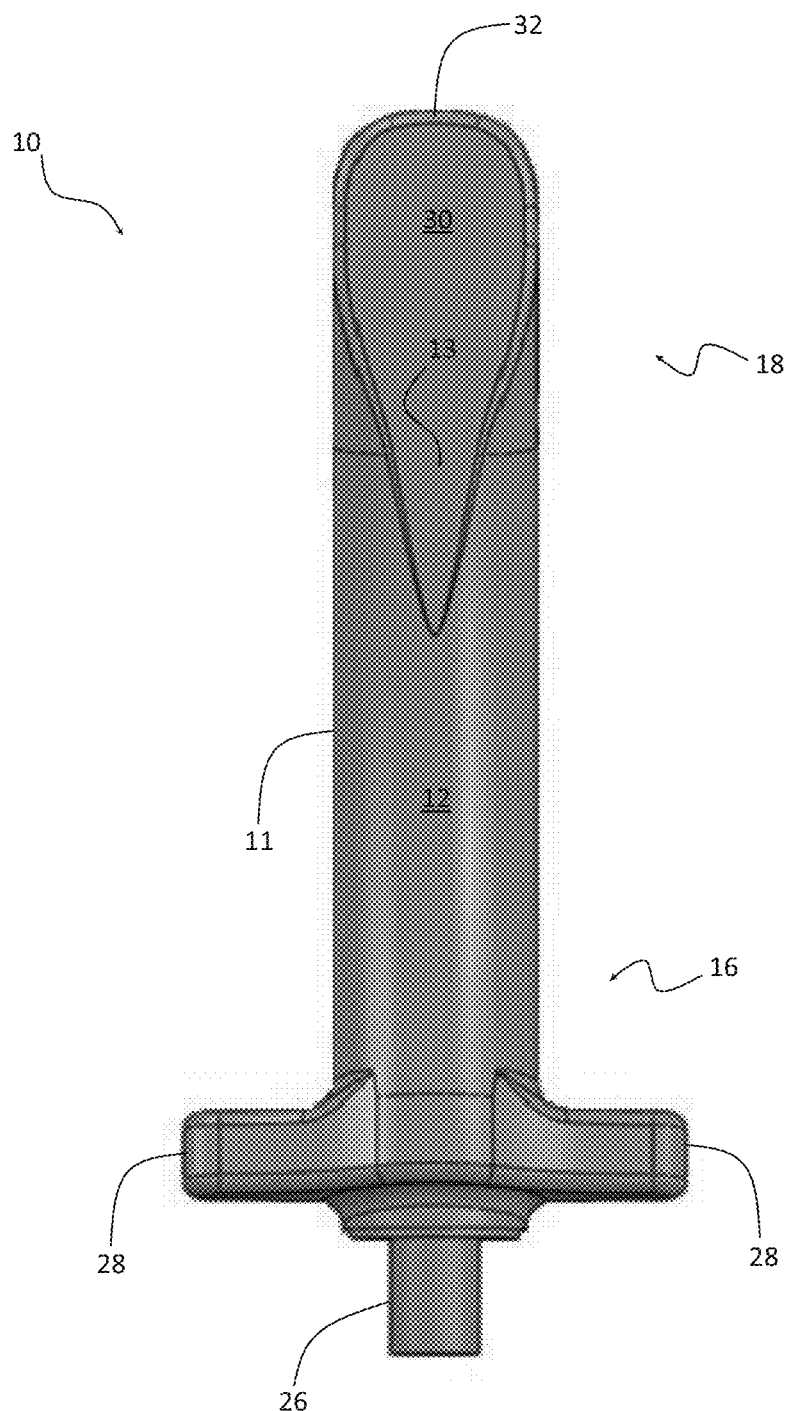
FIG. 2 is a top view of a transvaginal laparoscopic tool with obturator according to an embodiment of the current invention.

Port opening 30 can have any suitable shape and size. As seen in FIG. 2, port opening 30 can be generally teardrop-shaped with a wider width at its most distal position near lip 32 and a narrower width forming a point at its most proximal position. It can be appreciated that port opening 30 can have any suitable shape as needed or desired by a user. Examples include, but are not limited to, circular, ovular, diamond, and square, among other regular and irregular shapes.

Second side 14 is curved to enable easier and safer access into the peritoneal cavity to function as a vaginal laparoscopic port. Second side 14 is also designed with a curve that enables easier access into the posterior cul-de-sac (i.e., Pouch of Douglas). Additionally, the curve of second side 14 conforms to the conformation of the vagina when the patient is in a generally supine, lithotomy position (or similar position) utilized by a clinician to examine the pelvis or lower abdomen. In this position, the curve of second side 14 follows the path of the anterior vaginal wall and thus facilitates suturing of the Y-shaped sacrocolpopexy mesh (e.g., via interrupted permanent sutures, autosuture device) to the anterior vaginal wall against the solid surface of second side 14. This is particularly helpful since sacrocolpopexy mesh is intended to stretch the vagina longitudinally toward the sacrum.

Laparoscopic tool 10 can further include handles 28 that facilitate manipulation and control of tool 10. Handle 28 is positioned proximal to sheath 11 on proximal end 16 of laparoscopic tool 10. Any suitable handle or means of control can be utilized with laparoscopic tool 10.

Figure 4:
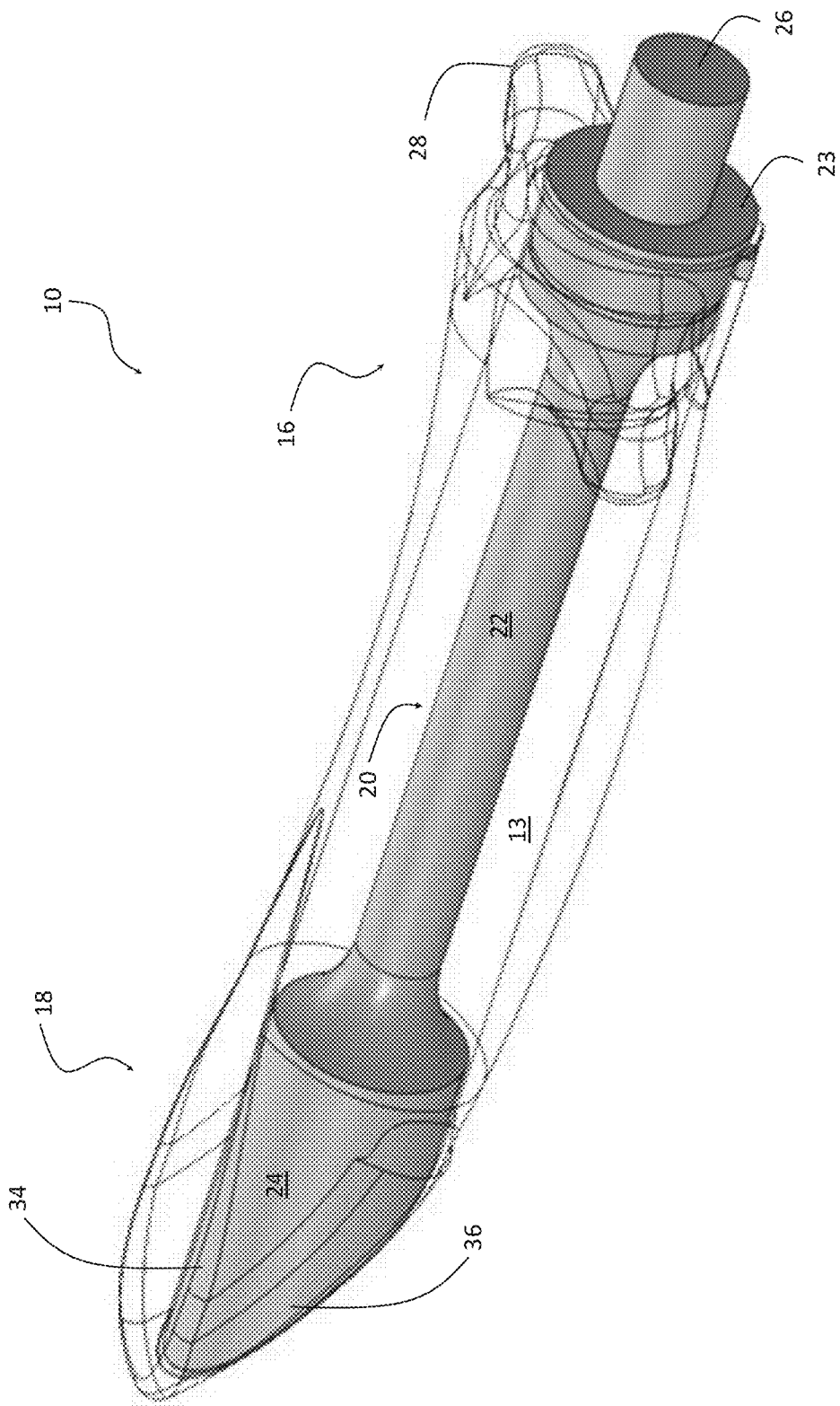
FIG. 4 is a wireframe view of an obturator within a transvaginal laparoscopic tool according to an embodiment of the current invention.

Obturator 20, which can be best seen in FIG. 4, is an elongate supplemental insertion component that is inserted into sheath 11 through proximal end 16 of laparoscopic tool 10. As seen in FIG. 4, obturator 20 can be formed of four main components: push/pull knob 26, connector 23, shaft 22, and head 24. When obturator 20 is inserted through sheath 11 within interstitial space 13, knob 26 can be positioned proximal to handles 28 and can be used to push or pull obturator 20 out of interstitial space 13 of sheath 11. Connector 23 is positioned within the interior of handles 28 and is connected to knob 26 on its proximal end. On its distal end, connector 23 is connected to the proximal end of shaft 22, such that connector 23 indirectly couples knob 26 with shaft 22. Alternatively, knob 26 can be coupled directly to shaft 22. Shaft 22 is longitudinally disposed through interstitial space 13 of sheath 11. This coupling/affixing of components can be accomplished via any means known in the art, for example including, but not limited to, thermal welding, electrical welding, soldering, or a pin hinge.

Head 24 is positioned at distal end 18 of laparoscopic tool 10 and is coupled to the distal end of shaft 22. Shaft 22 can have a width or diameter that is smaller than the width of head 24. This permits surgical instruments to access the patient's peritoneal cavity through port opening 30 even with obturator 20 inserted into sheath 11. This may be done if the operator or clinician desires port opening 20 to have a smaller size but still needs to access the peritoneal cavity with surgical instruments prior to blocking port opening 30 entirely.

Head 24 includes a first side, denoted by the reference numeral 34, and a second side, denoted by the reference numeral 36. First side 34 of obturator 20 is substantially flat and is aligned with first side 12 of sheath 11, substantially within port opening 30 when obturator 20 is positioned within interstitial space 13 of sheath 11. Second side 36 of obturator 20 is curved and is aligned with the curve of second side 14 of sheath 11 at proximal end 18 of laparoscopic tool 10. In other words, the curve of second side 36 of obturator 20 has a similar angle, arc, or curvature as the curve of second side 14 of sheath 11. This configuration allows head 24 to rest within distal end 18 of laparoscopic tool 10 while minimizing the space wasted within interstitial space 13.

Because first side 34 of obturator 20 is aligned within port opening 30 of first side 12 of sheath 11, obturator 20 blocks the space provided by port opening 30. When obturator 20 is blocking at least a portion of the space provided by port opening 30, obturator 20 can be utilized as a solid or firm surface against the posterior vaginal wall for sacrocolpopexy mesh to be sutured to the posterior vaginal wall. Additionally, the curves of second sides 14, 36 allow obturator 20 to be pushed further into interstitial space 13 of sheath 11. Obturator 20 can thus be used to reduce the size of port opening 30 into the peritoneal cavity. In turn, the port leading to the peritoneal cavity can be increased, decreased, or otherwise customized without changing the size or shape of laparoscopic tool 10.

Figure 3:
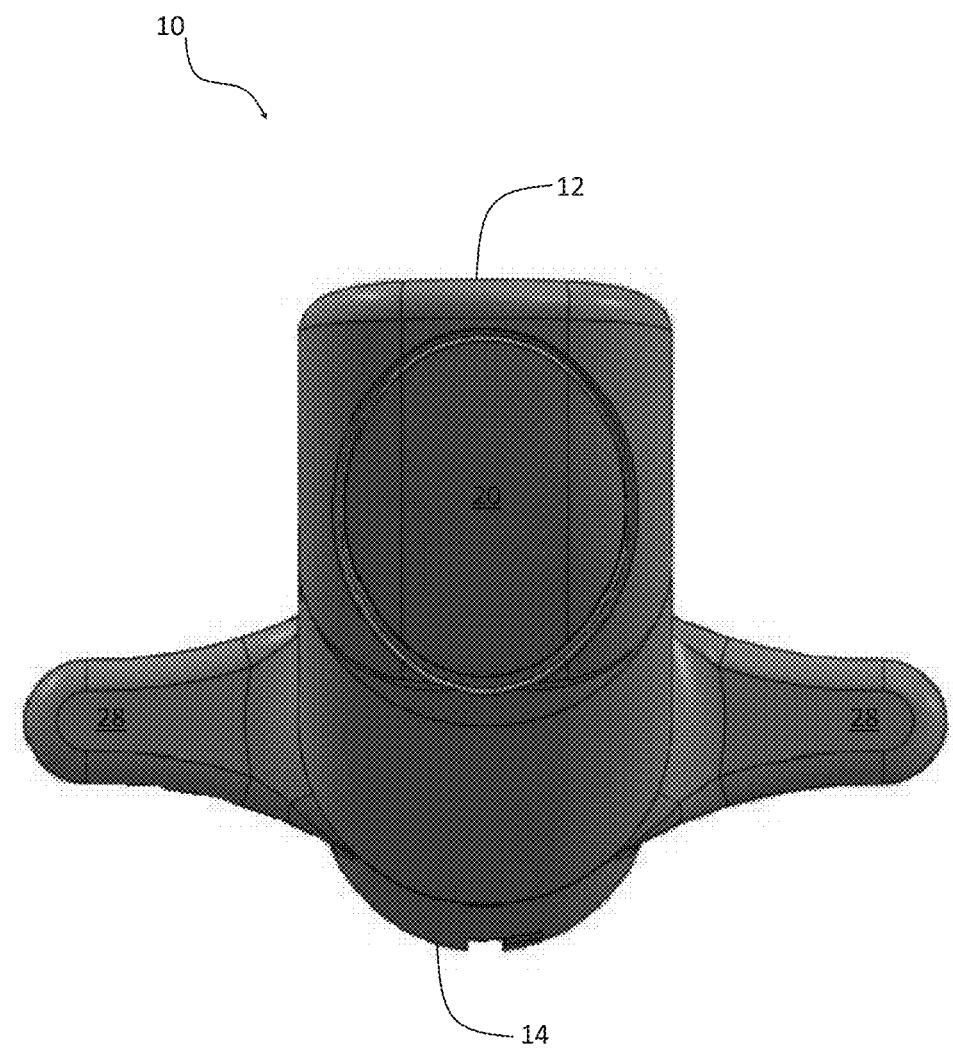
FIG. 3 is a rear view of a transvaginal laparoscopic tool with obturator according to an embodiment of the current invention.

FIGS. 3 and 4 depicts port opening 30 into the peritoneal cavity with obturator 20 in place to block, obstructs, or covers port opening 30, so that the Y-shaped sacrocolpopexy mesh can be sutured to the posterior vaginal wall on a firm surface (i.e., first surface 34 of head 24 of obturator 20). Obturator 20 can thus permit multiple size openings into the peritoneal cavity, allowing various size ports for the needs of different surgical procedures, and even placement of a sacrocolpopexy mesh fixation needle device through the vaginal wall to hold the Y-shaped mesh in place during suturing to the vaginal wall.

In an exemplary operation, distal end 18 of laparoscopic tool 10 is inserted into a vagina of a patient or subject using handles 28. Sheath 11 traverses the length of the vagina with port opening 30 of first side 12 facing or opening to the posterior vaginal wall and with second side 14 facing the anterior vaginal wall along its curve. When port opening 30 exposes the desired point of incision on the posterior vaginal wall (e.g., typically at the posterior cul-de-sac), interstitial space 13 of sheath 11 accommodates insertion of laparoscopic surgical tools (e.g., instruments, implants, sponges, needles or other objects) to make the appropriate incision and access the peritoneal cavity accordingly.

Sheath 11 and port opening 30 can be utilized as a laparoscopic port by itself to access the peritoneal cavity and lower abdomen of the patient. For example, a fluid (e.g., gas) can be pumped into the peritoneal cavity or lower abdomen to obtain and maintain pneumoperitoneum (e.g., using an air source providing carbon dioxide). Obturator 20 can then be inserted into the proximal end of sheath 11 in proximal end 16 of laparoscopic tool 10 if an operator or clinician requires a smaller port into the patient (e.g., for insertion of smaller laparoscopic instruments) or if the operator/clinician requires the peritoneal cavity of the patient to be sealed off from the external environment (i.e., exterior space), such as from interstitial space 13 (e.g., in order to maintain pneumoperitoneum or to suture sacrocolpopexy mesh to the posterior vaginal wall). Access to the posterior cul-de-sac can also be made by simply cutting through the vagina, posterior to the cervix, without requiring pneumoperitoneum.

When obturator 20 is blocking, covering, or otherwise obstructing port opening 30, access to the desired abdominal or pelvic region can be attained via known techniques, for example laparoscopic procedures through the patient's navel or other port. With obturator 20 in place, the operator or clinician can utilize obturator 20 within sheath 11 as a firm surface against which to suture sacrocolpopexy mesh to the posterior vaginal wall. With sheath 11 in place, the operator or clinician can utilize the curve of second side 14 as a firm surface against which to suture sacrocolpopexy mesh to the anterior vaginal wall. When the Y-shaped sacrocolpopexy mesh has been sutured to the anterior and posterior vaginal walls (and presumably to the sacrum), laparoscopic tool 10 can be removed from the patient's vagina.

Example 2

If needed, laparoscopic tool 10 can be inserted into the vagina with first side 12 positioned along or otherwise facing the anterior vaginal wall. This configuration would permit an incision to be made along the anterior vaginal wall through port opening 30. Further, when obturator 20 is inserted into sheath 11 through proximal end 16 of laparoscopic tool 10, obturator 20 can provide a solid surface that can be used to facilitate suturing sacrocolpopexy mesh to the anterior vaginal wall.

Example 3

Although the current specification has focused primarily on sacrocolpopexy procedures, it can be appreciated that the current invention has a structure that can be utilized for a variety of applications and procedures where access to the patient or subject's abdominal or pelvic region is desired.

With certain applications including the retrieval of large abdominal masses and transfer of surgical instruments into the abdominal cavity, the laparoscopic device has the potential to expand the use of the vaginal opening as a natural surgical orifice while preserving the use of small port sites during the laparoscopic surgery. This device allows for removal of larger specimens than is possible through the abdomen, without the need for morcellation of tissue or enlarging incisions in the abdominal wall to remove them.

Glossary of Claim Terms

Aligned or coplanar: This term is used herein to refer to two components of a structure being in line with each other or along the substantially same plane.

Branch: This term is used herein to refer to a prong of a Y-shaped mesh along the end of the mesh that includes two (2) distinct components or prongs that need to be sutured to the prolapsed anatomical structure.

Curvature: This term is used herein to refer to the measure, shape, or degree to which a surface is curved.

Curved: This term is used herein to refer to a characteristic of the invention, when viewed from at least one angle, has a generally crescent shape, with one edge having a concave shape and the opposite edge having a convex shape. The angulation of the curve, i.e., curvature, may vary, for example having a customized curvature.

Distal: This term is used herein to refer to a location that, during normal use, is farther from the clinician using the device and closer to the patient in connection with whom the device is used Interstitial space: This term is used herein to refer to a hollow space, i.e. not occupied by a solid, which is bound by one or more solids in two dimensions. For example, the interstitial space may have a square cross-section, which is bound in two dimensions by four walls. Alternatively, the interstitial space may have an oval or circular cross-section, which is bound in two dimensions by a tubular structure.

Laparoscopic: This term is used herein to encompass any minimally invasive surgical technique, including endoscopy and NOTES. The term is intended to be used in its broadest sense, and not limited to specific laparoscopic techniques.

Longitudinal side: This term is used herein to refer to a surface of a structure along the longitudinal axis of that structure.

Obturator: This term is used herein to refer to an apparatus or device used to block, cover, close, or otherwise obstruct a hole (e.g., port opening) partially or wholly. As used with the current invention, the obturator blocks, covers, closes, or otherwise obstructs the port opening formed in the sheath of the laparoscopic tool.

Ovoid: This term is used herein to refer to having a general oval structure, such as an egg-shape in three dimensions.

Patient: This term is used herein to refer to humans, but can also include any member of the animal kingdom, including mammals, such as but not limited to, primates including gorillas and monkeys; rodents, such as mice, fish, reptiles and birds. The patient may be any animal requiring any surgical therapy, treatment, or prophylaxis. The term treatment, as used in this definition only, is intended to mean that regiment described is continued until the underlying disease is resolved, whereas therapy requires that the regiment alleviate one or more symptoms of the underlying disease. Prophylaxis means that regiment is undertaken to prevent a possible occurrence, such as where a pre-cancerous lesion is identified.

Peritoneal cavity: This term is used herein to encompass the abdominal region and pelvic region of a patient, along with any other region that may be accessed via use of a laparoscopic tool.

Port opening: This term is used herein to refer to a regularly- or irregularly-shaped aperture that provides open or fluid communication between the interior of a structure (in which the port opening is formed) and the exterior environment.

Proximal: This term is used herein to refer to a location that, during normal use, is closer to the operator or clinician using the device and farther from the patient in connection with whom the device is used.

Push-pull knob: This term is used herein to refer to a protuberance, handle, or control switch that can be gripped or otherwise used to insert and retract the obturator from the sheath of the laparoscopic tool.

Semi-flat: This term is used herein to refer to a surface that is primarily planar but can otherwise have minor curvatures in order to form to the underlying tissue being contacts so as to provide a sealable fit between the surface and the tissue.

Substantially: This term is used herein to refer to characteristic being largely, if not wholly, that which is specified but so close that the difference is structurally or functionally insignificant.

User: This term is used herein to refer to any operator or clinician utilizing the laparoscopic tool of the current invention.

The advantages set forth above, and those made apparent from the foregoing disclosure, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

What is claimed is:

1. A method of treating pelvic organ prolapse in a female patient, comprising the steps of:
    inserting a laparoscopic tool into a vagina of said female patient, said laparoscopic tool including:
        a tubular or ovoid elongate sheath having a proximal end and a distal end, said elongate sheath further having a first longitudinal side and a second longitudinal side that enclose an interstitial space, said first longitudinal side being semi-flat and said second longitudinal side being curved,
        a teardrop-shaped port opening formed in said first longitudinal side at said distal end of said elongate sheath, said port opening having a wider width at its most distal point and a narrower width at its most proximal point, said port opening having a length along said first longitudinal side that is substantially aligned or coplanar with said first longitudinal side,
        a lip formed at a connection point between said first longitudinal side and said second longitudinal side, wherein said lip and said connection point are positioned distal to the distalmost end of said port opening,
        wherein said port opening opens in a direction normal to a length of said first longitudinal side;
    making an incision through said port opening where desired by a user;
    accessing a peritoneal cavity of said female patient through said incision;
    inserting an elongate obturator through said interstitial space of said elongate sheath to reduce the size of said port opening, said obturator including a shaft disposed within said interstitial space when said obturator is inserted into said elongate sheath, said obturator further including a head coupled to a distal end of said shaft, said head positioned at said distal end of said elongate sheath when said obturator is inserted into said elongate sheath, said shaft having a diameter or width that is smaller than a width of said head of said obturator,
    said head of said obturator having a first side and a second side, said first side of said head being substantially flat and aligning with a space or void provided by said port opening within said first longitudinal side of said elongate sheath, said second side being curved and disposed along said second longitudinal side of said sheath, said second side having a curvature that follows a curvature of said second longitudinal side of said elongate sheath and is similar to said curvature of said second longitudinal side of said elongate sheath at said distal end of said elongate sheath,
    wherein said obturator does not extend through said port opening due to being aligned with said space or void provided by said port opening; and
    suturing a sacrocolpopexy mesh to said vagina using said first side of said head of said obturator, said second side of said sheath, or a combination thereof as one or more firm surfaces against which said user can suture said sacrocolpopexy mesh to said vagina.

2. A method of treating pelvic organ prolapse as in claim 1, further comprising:
    said sacrocolpopexy mesh being a Y-shaped mesh with two (2) branches on an end of said Y-shaped mesh.

3. A method of treating pelvic organ prolapse as in claim 2, further comprising the steps of:
    during insertion of said laparoscopic tool in said vagina of said female patient, positioning said semi-flat side of said sheath and said port opening against a posterior vaginal wall of said vagina;
    during insertion of said laparoscopic tool in said vagina of said female patient, positioning said curved side of said sheath against an anterior vaginal wall of said vagina;
    suturing a first branch of said two (2) branches of said Y-shaped mesh against said posterior vaginal wall using said substantially flat side of said head of said obturator as a first firm surface against which said user can suture said first branch of said Y-shaped mesh to said posterior vaginal wall; and
    suturing a second branch of said two (2) branches of said Y-shaped mesh against said anterior vaginal wall using said curved side of said head of said obturator as a second firm surface against which said user can suture said second branch of said Y-shaped mesh to said anterior vaginal wall.

4. A method of treating pelvic organ prolapse as in claim 1, further comprising:
    said incision made in a posterior cul-de-sac of said female patient through said port opening of said laparoscopic tool in order to access said peritoneal cavity of said female patient.

5. A method of treating pelvic organ prolapse as in claim 1, further comprising:

said laparoscopic tool further including a push-pull knob coupled to a proximal end of said shaft of said obturator for pushing or pulling said obturator into and out of said elongate sheath.

6. A method of treating pelvic organ prolapse as in claim 1, further comprising:
said laparoscopic tool further including a handle connected to said proximal end of said elongate sheath for controlling said laparoscopic tool.

7. A method of treating pelvic organ prolapse as in claim 1, further comprising:
prior to the step of inserting said obturator, utilizing said sheath and said port opening as a laparoscopic port to access said peritoneal cavity of said female patient.

8. A method of treating pelvic organ prolapse as in claim 7, further comprising:
pumping a fluid into said peritoneal cavity through said laparoscopic port.

9. A method of treating pelvic organ prolapse as in claim 1, further comprising:
accessing a posterior cul-de-sac of said female patient by making an incision through said vagina at a position posterior to a cervix of said female patient, without requiring pneumoperitoneum.

10. A method of treating pelvic organ prolapse as in claim 1, further comprising:
removing said laparoscopic tool from said vagina of said female patient after the step of suturing said sacrocolpopexy mesh to said vagina.

* * * * *